United States Patent [19]

Behrens et al.

[11] Patent Number: 5,112,890

[45] Date of Patent: * May 12, 1992

[54] STABILIZATION OF ACID CATALYZED THERMOSET RESINS

[75] Inventors: Rudolf A. Behrens, New Fairfield, Conn.; Roland A. E. Winter, Armonk, N.Y.; Andrew Mar, Norwalk, Conn.; Peter J. Schirmann, Fairfield, Conn.; Raymond Seltzer, New City, N.Y.; Roger F. Malherbe, Basel, Switzerland

[73] Assignee: Ciba-Geigy Corporation, Ardsley, N.Y.

[ * ] Notice: The portion of the term of this patent subsequent to Apr. 24, 2007 has been disclaimed.

[21] Appl. No.: 259,952

[22] Filed: Oct. 19, 1988

Related U.S. Application Data

[63] Continuation-in-part of Ser. No. 99,411, Sep. 21, 1987, abandoned.

[51] Int. Cl.$^5$ .................. C08K 34/15; C08K 34/35
[52] U.S. Cl. ...................................... 524/95; 524/99; 524/100; 524/101; 524/102; 524/103

[58] Field of Search .............. 524/95, 99, 100, 101, 524/102, 103; 544/198, 351, 383, 389; 546/19, 20, 186, 188, 189, 245

[56] References Cited

U.S. PATENT DOCUMENTS

| 4,148,784 | 4/1979 | Malherbe et al. | 524/102 |
| 4,314,933 | 2/1982 | Berner | 524/102 |
| 4,426,471 | 1/1984 | Berner | 524/102 |
| 4,472,547 | 7/1984 | Malherbe | 524/98 |
| 4,691,015 | 9/1987 | Behrens et al. | 529/102 |

FOREIGN PATENT DOCUMENTS 1196444 11/1985 Canada .................. 524/102

OTHER PUBLICATIONS

Shlyapintokh et al. "Developements in Polymer Stabilisation", V, 41-70 [1982].
Journal of Polymer Science, Polymer Chemistry Ed., 22, 277-281 (1984).

Primary Examiner—Kriellion S. Morgan

[57] ABSTRACT

N-OR$_1$ substituted hindered amine light stabilizers impart outstanding stabilization properties to acid catalyzed thermoset coating compositions providing enhanced resistance against the deleterious effects of light, moisture or oxygen without inhibition of cure.

27 Claims, No Drawings

STABILIZATION OF ACID CATALYZED THERMOSET RESINS

BACKGROUND OF THE INVENTION

The instant invention pertains to the stabilization of acid catalyzed thermosetting resins as used in baked enamels or stoving lacquers by use of hindered amine light stabilizers substituted on the hindered nitrogen atom by a variety of $OR_1$ groups.

Hindered amine light stabilizers are well known to be effective in stabilizing a host of organic substrates including polymers from the deleterious effects of oxygen and light.

Such hindered amine light stabilizers have been used in the stabilization of hot-crosslinkable alkyd or acrylic metallic stoving lacquers (U.S. Pat. No. 4,426,472) and in stabilizing acid-catalyzed stoving lacquers based on hot-crosslinkable acrylic polyester or alkyd resins (U.S. Pat. Nos. 4,344,876 and 4,426,471). None of the hindered amine light stabilizers of these patents possess structures having an O-substituted hydroxyl group substituted directly on the N-atom of the hindered amine.

In their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

THE INVENTION

The present invention relates to the use of N-$OR_1$-substituted 2,2,6,6-tetraalkylpiperidine or piperazine compounds, optionally together with further stabilizers for protecting acid-catalyzed thermosetting resins such as acrylic, polyester, polyurethane, polyamide or alkyd resins against the action of light, moisture, and oxygen.

The compounds of the present invention are less basic than the corresponding hindered amine compounds from which they are derived, yet still exhibit undiminished, indeed enhanced, light stabilization efficacy.

The aforementioned problems encountered with use of compounds having a basic N-atom with acid catalyzed thermoset enamels were addressed in U.S. Pat. Nos. 4,344,876 and 4,426,471. Substitution of the N-atom of the hindered amines with an inert blocking group such as alkyl, alkenyl, benzyl, alkanoyl and the like clearly mitigated the difficulties and led to acid catalyzed thermoset enamels having acceptable light stabilization properties.

Substitution of the hindered N-atom of the hindered amines by $OR_1$ groups as per the instant invention provides even better light stabilization effects for the acid catalyzed thermoset enamels.

The present invention is concerned with the stabilization of acid catalyzed stoving lacquers based on hot crosslinkable acrylic, polyester, polyurethane, polyamide or alkyd resins against the action of light and moisture by the addition of substituted polyalkylpiperidine or other hindered amine derivatives, and with the stabilized acid catalyzed thermosetting resins thereby obtained.

On occasion, but especially in repairing finishes and lacquers with a high solids content (generally greater than 50%, by weight) for use in industrial finishes, thermoset systems based on hot crosslinkable acrylic, modified acrylic, e.g. acrylic polyurethane, polyester, siliconized polyesters, polyester urethane or alkyd resins are provided with an additional acid catalyst. In such instances, however, failure symptoms caused by salt formation between light stabilizer and acid catalyst, delays in hardening, pigment flocculation and reduced light protective action are observed. These problems can be solved in a most satisfactory manner by means of the inventive use of the instant substituted polyalkylpiperidine derivatives.

Accordingly, the present invention relates to the use of N-$OR_1$-substituted 2,2,6,6-tetraalkylpiperidine compounds, optionally together with further stabilizers, for stabilizing acid catalyzed baking finishes or coatings or thermoset coatings based on hot crosslinkable acrylic, modified acrylic, polyester, modified polyester or alkyd resins, in particular acrylic, polyester, polyurethane, polyamide or alkyd resins, against the action of light, moisture and oxygen.

The N-$OR_1$-substituted hindered amine compounds of this invention contain a group of the formula

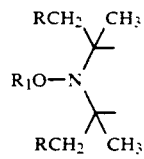

wherein R is hydrogen or methyl, and $R_1$ is $C_1$-$C_{18}$ alkyl, $C_2$-$C_{18}$ alkenyl, $C_2$-$C_{18}$ alkynyl, $C_5$-$C_7$ cycloalkyl, $C_6$-$C_{10}$ bicycloalkyl, $C_5$-$C_8$ cycloalkenyl, $C_6$-$C_{10}$ aryl, $C_7$-$C_9$ aralkyl, $C_7$-$C_9$ aralkyl substituted by alkyl or aryl, or

wherein D is $C_1$-$C_{18}$ alkyl, $C_1$-$C_{18}$ alkoxy, phenyl, phenyl substituted by hydroxy, alkyl or alkoxy, or amino or amino mono- or disubstituted by alkyl or phenyl, Some are known compounds while others are claimed in copending applications Ser. Nos. 99,414, now abandoned, and 99,419, now abandoned.

More particularly, the instant invention relates to a derivative having one of formulae A to P

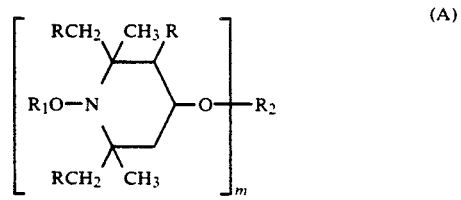
(A)

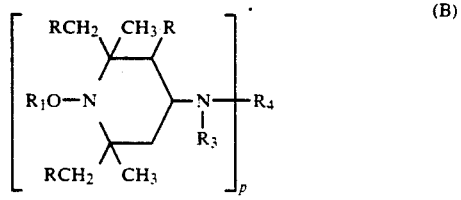
(B)

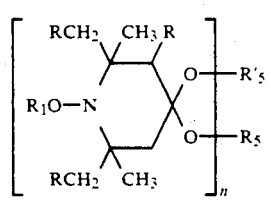
(C)
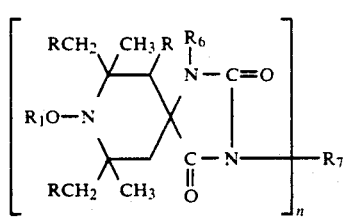
(D)
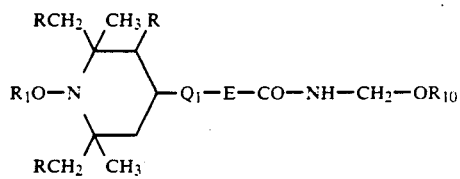
(E)
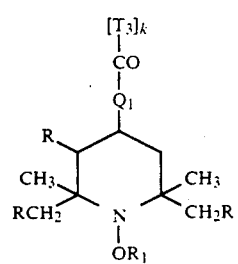
(F)
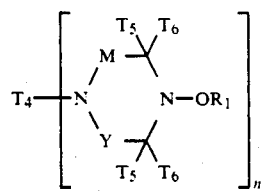
(G)
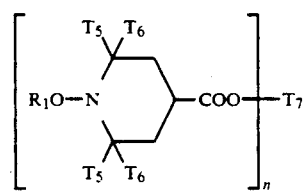
(H)
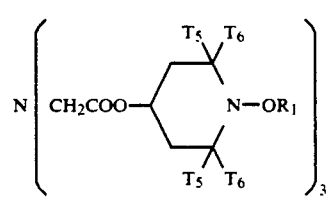
(I)
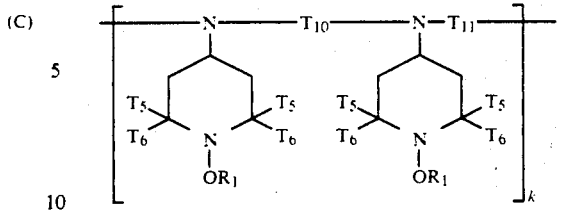
(J)
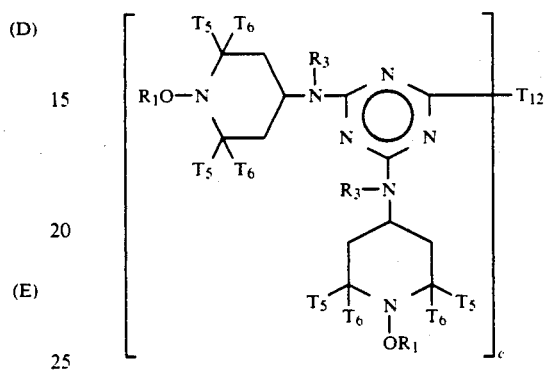
(K)
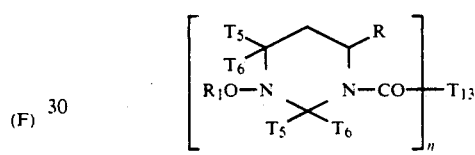
(L)
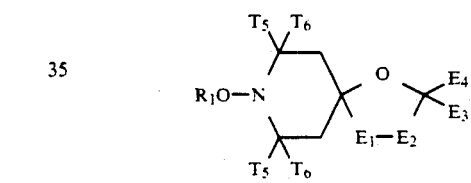
(M)
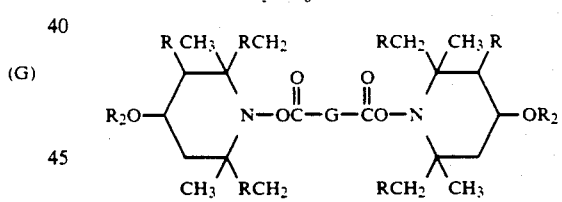
(N)
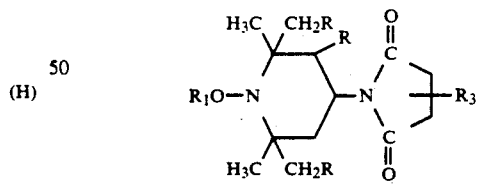
(O)
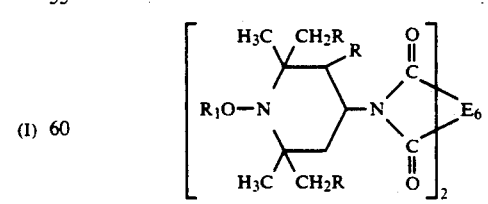
(P)
wherein
R is hydrogen or methyl,
$R_1$ is independently $C_1$-$C_{18}$ alkyl, $C_2$-$C_{18}$ alkenyl, $C_2$-$C_{18}$ alkynyl, $C_5$-$C_{12}$ cycloalkyl, $C_6$-$C_{10}$ bicycloalkyl, C5–C8 cycloalkenyl, C6–C10 aryl, C7–C9 aralkyl, C7–9 aralkyl substituted by alkyl or aryl, or

wherein D is C1–C18 alkyl, C1–C18 alkoxy, phenyl, phenyl substituted by hydroxy, alkyl or alkoxy, or amino or amino mono- or disubstituted by alkyl or phenyl;

m is 1–4, when m is 1,

R2 is hydrogen, C1–C18 alkyl optionally interrupted by one or more oxygen atoms, C2–C12 alkenyl, C6–C10 aryl, C7–C18 aralkyl, glycidyl, a monovalent acyl radical of an aliphatic, cycloaliphatic, araliphatic or aromatic carboxylic acid, or of a carbamic acid, preferably an acyl radical of an aliphatic carboxylic acid having 2–18 C atoms, of a cycloaliphatic carboxylic acid having 5–12 C atoms or of an aromatic carboxylic acid have 7–15 C atoms, or

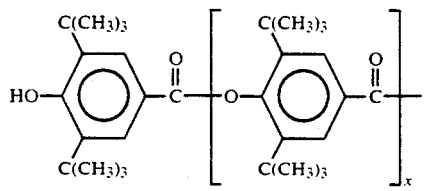

wherein x is 0 or 1, or

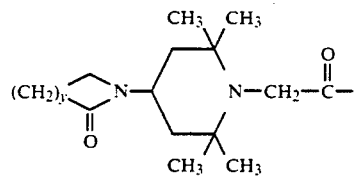

wherein y is 2–4;

when m is 2,

R2 is C1–C12 alkylene, C4–C12 alkenylene, xylylene, a divalent acyl radical of an aliphatic, cycloaliphatic, araliphatic or aromatic dicarboxylic acid or of a dicarbamic acid, preferably an acyl radical of an aliphatic dicarboxylic acid having 2–18 C atoms, of a cycloaliphatic or aromatic dicarboxylic acid having 8–14 C atoms, or of an aliphatic, cycloaliphatic or aromatic dicarbamic acid having 8–14 C atoms;

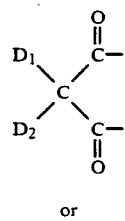

or

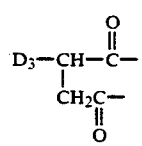

-continued
or

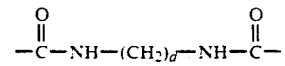

wherein D1 and D2 are independently hydrogen, an alkyl radical containing up to 8 carbon atoms, an aryl or aralkyl radical including 3,5-di-t-butyl-4-hydroxybenzyl radical, D3 is hydrogen or an alkyl or alkenyl radical containing up to 18 carbon atoms, and d is 0–20;

when m is 3, R2 is a trivalent acyl radical of an aliphatic, unsaturated aliphatic, cycloaliphatic, or aromatic tricarboxylic acid;

when m is 4, R2 is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;

p is 1, 2 or 3,

R3 is hydrogen, C1–C12 alkyl, C5–C7 cycloalkyl, C7–C9 aralkyl, C2–C18 alkanoyl, C3–C5 alkenoyl or benzoyl;

when p is 1,

R4 is hydrogen, C1–C18 alkyl, C5–C7 cycloalkyl, C2–C8 alkenyl unsubstituted or substituted by a cyano, carbonyl or carbamide group, aryl, aralkyl, or it is glycidyl, a group of the formula —CH2—CH(OH)—Z or of the formula —CO—Z or —CONH—Z wherein Z is hydrogen, methyl or phenyl; or a group of the formulae

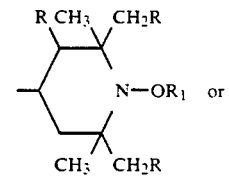

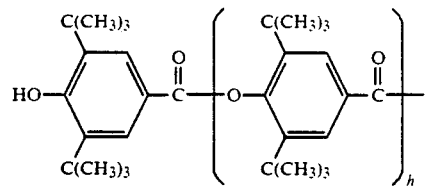

with h as 0 or 1;

or R3 and R4 together when p is 1 can be alkylene of 4 to 6 carbon atoms or 2-oxopolyalkylene or the cyclic acyl radical of an aliphatic or aromatic 1,2- or 1,3-dicarboxylic acid, when p is 2, R4 is a direct bond or is C1–C12 alkylene, C6-C12 arylene, xylylene, a —CH2CH(OH)—CH2 group, or a group —CH2—CH(OH)—CH2—O—X—O—CH2—CH(OH)—CH2— wherein X is C2–C10 alkylene, C6–C15 arylene or C6–C12 cycloalkylene; or, provided that R3 is not alkanoyl, alkenoyl or benzoyl, R4 can also be a divalent acyl radical of an aliphatic, cycloaliphatic or aromatic dicarboxylic acid or dicarbamic acid, or can be the group —CO—; or R4 is

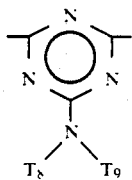

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, preferably $T_8$ and $T_9$ together are 3-oxapentamethylene;

when p is 3, $R_4$ is 2,4,6-triazinyl, n is 1 or 2, when n is 1, $R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or hydroxyalkylene or $C_4$-$C_{22}$ acyloxyalkylene;

when n is 2, $R_5$ and $R'_5$ together are $(-CH_2)_2C(CH_2-)_2$;

$R_6$ is hydrogen, $C_1$-$C_{12}$ alkyl, allyl, benzyl, glycidyl or $C_2$-$C_6$ alkoxyalkyl;

when n is 1, $R_7$ is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula $-(CH_2)_t-COO-Q$ or of the formula $-(CH_2)_t-O-CO-Q$ wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group $-CH_2CH(OH)-CH_2-O-X-O-CH_2-CH(OH)-CH_2-$ wherein X is $C_2$-$C_{10}$ alkylene, $C_6$-$C_{15}$ arylene or $C_6$-$C_{12}$ cycloalkylene, or a group $-CH_2CH(OZ')CH_2-(OCH_2-CH(OZ')CH_2)_2-$ wherein Z' is hydrogen, $C_1$-$C_{18}$ alkyl, allyl, benzyl, $C_2$-$C_{12}$ alkanoyl or benzoyl;

Q is $-N(R_8)-$ or $-O-$; E is $C_1$-$C_3$ alkylene, the group $-CH_2-CH(R_9)-O-$ wherein $R_9$ is hydrogen, methyl or phenyl, the group $-(CH_2)_3-NH-$ or a direct bond;

$R_{10}$ is hydrogen or $C_1$-$C_{18}$ alkyl, $R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group $-CH_2-CH(R_9)-OH$ wherein $R_9$ has the meaning defined above; a group of the formula

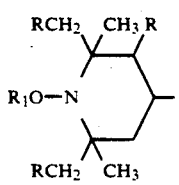

or a group of the formula

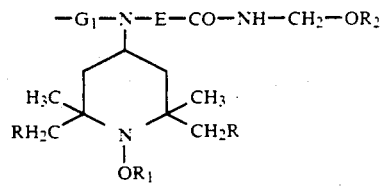

wherein $G_1$ can be $C_2$-$C_6$ alkylene or $C_6$-$C_{12}$ arylene; or $R_8$ is a group $-E-CO-NH-CH_2-OR_{10}$;

Formula F denotes a recurring structural unit of a polymer where $T_3$ is ethylene or 1,2-propylene, or is the repeating structural unit derived from an alpha-olefin copolymer with an alkyl acrylate or methacrylate; preferably a copolymer of ethylene and ethyl acrylate, and where k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene, preferably $T_5$ and $T_6$ are each methyl, M and Y are independently methylene or carbonyl preferably M is methylene and Y is carbonyl, and $T_4$ is ethylene where n is 2;

$T_7$ is the same as $R_7$, and $T_7$ is preferably octamethylene where n is 2, $T_{10}$ and $T_{11}$ are independently alkylene of 2 to 12 carbon atoms, or $T_{11}$ is

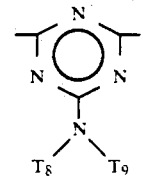

$T_{12}$ is piperazinyl, $$-NR_{11}-(CH_2)_d-NR_{11}- \quad \text{or}$$

$$-NH(CH_2)_a-N(CH_2)_b-N[(CH_2)_c-N]_fH$$

where $R_{11}$ is the same as $R_3$ or is also

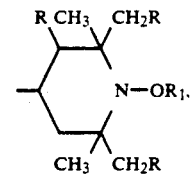

a, b and c are independently 2 or 3, and f is 0 or 1, preferably a and c are each 3, b is 2 and f is 1; and e is 2, 3 or 4, preferably 4;

$T_{13}$ is the same as $R_2$ with the proviso that $T_{13}$ cannot be hydrogen when n is 1;

$E_1$ and $E_2$, being different, each are $-CO-$ or $-N(E_5)-$ where $E_5$ is hydrogen, $C_1$-$C_{12}$ alkyl or $C_4$-$C_2$ alkoxycarbonyl-alkyl, preferably $E_1$ is $-CO-$ and $E_2$ is $-N(E_5)-$, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, and $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl;

$R_2$ of formula (N) is as previously defined when m is 1, G is a direct bond, $C_1$-$C_{12}$ alkylene, phenylene or —NH—G'—NH wherein G' is $C_1$-$C_{12}$ alkylene, and $E_6$ is an aliphatic or aromatic tetravalent radical.

In the structures A to N, if any substituents are $C_1$-$C_{18}$ alkyl they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl, cyclohexyl and cyclododecyl; typical cycloalkenyl groups include cyclohexenyl; while typical aralkyl groups include benzyl, alpha-methylbenzyl, alpha,alpha-dimethylbenzyl or phenethyl. $C_1$-$C_{12}$ alkyl and cyclohexyl are preferred.

If $R_2$ is a monovalent acyl radical of a carboxylic acid, it is for example an acyl radical of acetic acid, stearic acid, salicylic acid, benzoic acid or β-(3,5-di-tert-butyl-4-hydroxyphenyl) propionic acid.

If $R_2$ is a divalent acyl radical of a dicarboxylic acid, it is for example an acyl radical of oxalic acid, adipic acid, succinic acid, suberic acid, sebacic acid, phthalic acid, maleic acid, dibutylmalonic acid, dibenzylmalonic acid or butyl-(3,5-di-tert-butyl-4-hydroxybenzyl)-malonic acid, or bicycloheptenedicarboxylic acid, with succinates, sebacates, phthalates, and isophthalates being preferred.

If $R_2$ is a divalent acyl radical of a dicarbamic acid, it is for example an acyl radical of hexamethylenedicarbamic acid or of 2,4-toluylenedicarbamic acid.

The following compounds are examples of polyalkylpiperidine starting materials useful in making the hydroxylamine derivatives of formula A.
4-benzyloxy-2,2,6,6-tetramethylpiperidine
4-acryloyloxy-2,2,6,6-tetramethylpiperidine
4-hydroxy-2,2,6,6-tetramethylpiperidine
4-stearoyloxy-2,2,6,6-tetramethylpiperidine
di-(2,2,6,6-tetramethylpiperidin-4-yl) adipate
di-(2,2,6,6-tetramethylpiperidin-4-yl) sebacate
di-(2,2,6,6-tetramethylpiperidin-4-yl)phthalate alpha,alpha'-(di-2,2,6,6-tetramethylpiperidine-4-oxy)-p-xylene
di-(2,2,6,6-tetramethylpiperidin-4-yl)succinate
di-(2,2,6,6-tetramethylpiperidin-4-yl)malonate
1,4-dihydroxy-2,2,6,6-tetramethylpiperidine
1-acetoxy-4-hydroxy-2,2,6,6-tetramethylpiperidine
(2,2,6,6-tetramethylpiperidin-4-yl)-[4-(2-oxoazepin-1-yl) -2,2,6,6-tetramethylpiperidin-4-yl]acetate.

As $C_7$-$C_9$ aralkyl, $R_3$ is particularly phenethyl or above all benzyl.

As $C_2$-$C_{18}$ alkanoyl, $R_3$ is for example propionyl, butyryl, octanoyl, dodecanoyl, hexadecanoyl, octadecanoyl, but preferably acetyl.

If $R_4$ is $C_2$-$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$-$C_{12}$ alkylene, they are for example ethylene, propylene, 2,2-dimethylpropylene, tetramethylene, hexamethylene, octamethylene, decamethylene or dodecamethylene.

If any substituents are $C_6$-$C_{15}$ arylene, they are for example o-, m- or p-phenylene, 1,4-naphthylene or 4,4'-diphenylene.

As $C_6$-$C_{12}$ cycloalkylene, X is especially cyclohexylene.

The following compounds are examples of polyalkylpiperidine starting materials useful in making the hydroxylamine derivatives of formula B.
N,N'-bis(2,2,6,6-tetramethylpiperidin-4-yl)-hexamethylene-1,6-diamine,
N,N'-bis-(2,2,6,6-tetramethylpiperidin-4-yl)-hexamethylene-1,6-diacetamide,
4-benzylamino-2,2,6,6-tetramethylpiperidine,
N-n-butyl-N-(2,2,6,6-tetramethylpiperidin-4-yl)-4-hydroxy-3,5-di-tert.butyl benzamide,
N,N'-bis-(2,2,6,6-tetramethylpiperidin-4-yl)-N,N'-dibutyl-adipamide,
N,N'-bis-(2,2,6,6-tetramethylpiperidin-4-yl)-N,N'-dicyclohexyl-(2-hydroxypropylene-diamine),
4-(3-methyl-4-hydroxy-5-tert-butyl-benzoyl acetamido)-2,2,6,6-tetramethylpiperidine,
alpha-cyano-β-methyl-β-[N-(2,2,6,6-tetramethylpiperidin-4-yl]-amino-acrylic acid methyl ester,
1-acetoxy-N-butylamino-2,2,6,6-tetramethyl piperidine,
1-oxyl-2,2,6,6-tetramethylpiperin-4-one.

If $R_5$ is $C_2$-$C_8$ alkylene or hydroxyalkylene, it is for example ethylene, 1-methyl-ethylene, propylene, 2-ethylpropylene or 2-ethyl-2-hydroxymethylpropylene.

As $C_4$-$C_{22}$ acyloxyalkylene, $R_5$ is for example 2-ethyl-2-acetoxymethyl-propylene.

The following compounds are examples for polyalkylpiperidine starting materials useful in making the hydroxylamine derivatives of formula C.
9-aza-8,8,10,10-tetramethyl-1,5-dioxaspiro[5.5]undecane,
9-aza-8,8,10,10-tetramethyl-3-ethyl-1,5-dioxaspiro[5.5]undecane,
2,2,6,6-tetramethylpiperidine-4-spiro-2'-(1', 3-dioxane) -5'-spiro-5''-(1'', 3''-dioxane)-2''-spiro-4'''-(2''', 2'''-6''',6'''-tetramethylpiperidine).

If any substituents are $C_2$-$C_6$ alkoxyalkyl, they are for example methoxymethyl, ethoxymethyl, propoxymethyl, tert-butoxyethyl, ethoxyethyl, ethoxypropyl, n-butoxyethyl, tert-butoxyethyl, isopropoxyethyl or propoxypropyl.

If $R_7$ is $C_3$-$C_5$ alkenyl, it is for example 1-propenyl, allyl, methallyl, 2-butenyl or 2-pentenyl.

As $C_7$-$C_9$ aralkyl, $R_7$ is in particular phenethyl or above all benzyl; and as $C_5$-$C_7$ cycloalkyl, $R_7$ is especially cyclohexyl.

If $R_7$ is $C_2$-$C_4$ hydroxyalkyl, it is for example 2-hydroxyethyl, 2-hydroxypropyl, 3-hydroxypropyl, 2-hydroxybutyl or 4-hydroxybutyl.

As $C_6$-$C_{10}$ aryl, $R_7$ is in particular phenyl, or alpha-or β-naphthyl which is unsubstituted or substituted by halogen or $C_1$-$C_4$ alkyl.

If $R_7$ is $C_2$-$C_{12}$ alkylene, it is for example ethylene, propylene, 2,2-dimethylpropylene, tetramethylene, hexamethylene, octamethylene, decamethylene or dodecamethylene.

If $R_7$ is $C_6$-$C_{12}$ arylene, it is for example o-, m- or p-phenylene, 1,4-naphthylene or 4,4'-diphenylene.

If Z' is $C_2$-$C_{12}$ alkanoyl, it is for example propionyl, butyryl, octanoyl, dodecanoyl or preferably acetyl.

The following compounds are examples of polyalkyl-piperidine starting materials useful in making hydroxylamine derivatives of formula D.

3-benzyl-1,3,8-triaza-7,7,9,9-tetramethylspiro[4.5]-decane-2,4-dione, 3-n-octyl-1,3,8-triaza-7,7,9,9-tetramethylspiro[4.5]-decane-2,4-dione, 3-allyl-1,3,8-triaza-1,7,7,9,9-pentamethylspiro[4.5]-decane-2,4-dione, or the compounds of the following formulae:

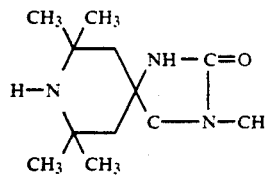

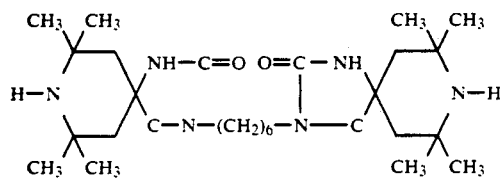

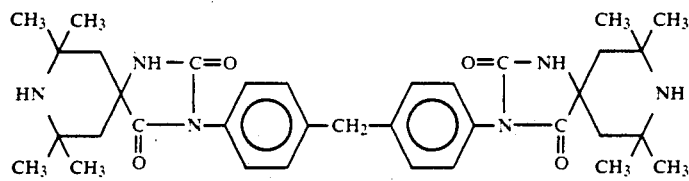

As $C_5-C_7$ cycloalkyl, $R_8$ is in particular cyclohexyl.

As $C_6-C_{10}$ aryl, $R_8$ is particularly phenyl, or alpha-or β-naphthyl which is unsubstituted or substituted with halogen or $C_1-C_4$ alkyl.

As $C_1-C_3$ alkylene, E is for example methylene, ethylene or propylene.

As $C_2-C_6$ alkylene, $G_1$ is for example ethylene, propylene, 2,2-dimethylpropylene, tetramethylene or hexamethylene; and as $C_6-C_{12}$ arylene, $G_1$ is o-, m- or p-phenylene, 1,4-naphthylene or 4,4'-diphenylene.

The following compounds are examples of polyalkyl-piperidine starting materials useful in making the hydroxylamine derivatives of formula E.

N-hydroxymethyl-N'-2,2,6,6-tetramethylpiperidin-4-yl-urea

N-methoxymethyl-N'-2,2,6,6-tetramethylpiperidin-4-yl

N-methoxymethyl-N'-n-dodecyl-N'-2,2,6,6-tetramethylpiperidin-4-yl-urea, and

O-(2,2,6,6-tetramethylpiperidin-4-yl)-N-methoxymethylurethane.

When the instant hydroxylamine derivatives is of formula F, the following polymeric compounds are examples of starting materials useful in preparing said derivatives.

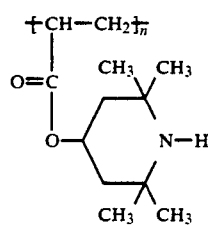

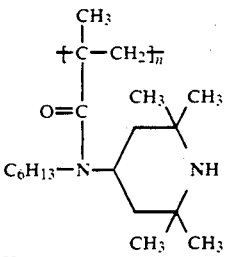

Additional starting hindered amine derivatives include for formula J:

poly-{[6-[(1,1,3,3-tetramethylbutyl)-imino]-1,3,5-triazine-2,4-diyl][2-(1-oxyl-2,2,6,6-tetramethylpiperidyl)-imino]-hexamethylene-4[4-(1-oxyl-2,2,6,6-tetra-methylpiperidyl]-imino]}.

For compounds of formula 0, $R_3$ is preferably $C_1-C_{12}$ alkyl and $C_5-C_7$ cycloalkyl and more preferably methyl, octyl, dodecyl and cyclohexyl.

For compounds of formula P, the following species are typical of tetracarboxylic acid dianhydrides suitable for the preparation thereof:

2,3,9,10-perylene tetracarboxylic acid dianhydride 1,4,5,8-naphthalene tetracarboxylic acid dianhydride 2,6-dichloronaphthalene-1,4,5,8-tetracarboxylic acid dianhydride 2,7-dichloronaphthalene-1,4,5,8-tetracarboxylic acid dianhydride 2,3,6,7-tetrachloronaphthalene-1,4,5,8-tetracarboxylic acid dianhydride phenanthrene-1,8,9,10-tetracarboxylic acid dianhydride 2,3,3', 4'-benzophenonetetracarboxylic acid dianhydride pyromellitic dianhydride 3,3', 4,4'-benzophenonetetracarboxylic acid dianhydride 2,2', 3,3'-benzophenonetetracarboxylic acid dianhydride 3,3', 4,4'-biphenyltetracarboxylic acid dianhydride 2,2', 3,3'-biphenyltetracarboxylic acid dianhydride 4,4'-isopropylidenediphthalic anhydride 3,3'-isopropylidenediphthalic anhydride 4,4'-oxydiphthalic anhydride
4,4'-sulfonyldiphthalic anhydride
3,3'-oxydiphthalic anhydride
4,4'-methylenediphthalic anhydride
4,4'-thiodiphthalic anhydride
4,4'-ethylidenediphthalic anhydride
2,3,6,7-naphthalenetetracarboxylic acid dianhydride
1,2,4,5-naphthalenetetracarboxylic acid dianhydride
1,2,5,6-naphthalenetetracarboxylic acid dianhydride
benzene-1,2,3,4-tetracarboxylic acid dianhydride
pyrazine-2,3,5,6-tetracarboxylic acid dianhydride.

The following compounds are examples of hydroxylamines derivatives applicable for use in the invention:

1. di-(1-acetoxy-2,2,6,6-tetramethylpiperidin-4-yl)-phthalate
2. di-(1-acetoxy-2,2,6,6-tetramethylpiperidin-4-yl)-isophthalate
3. di-(1-acetoxy-2,2,6,6-tetramethylpiperidin-4-yl) sebacate
4. di-(1-acetoxy-2,2,6,6-tetramethylpiperidin-4-yl) succinate
5. di-(1-acetoxy-2,2,6,6-tetramethylpiperidin-4-yl) adipate
6. di-(1-acetoxy-2,2,6,6-tetramethylpiperidin-4-yl) n-butylmalonate
7. di-(1-acetoxy-2,2,6,6-tetramethylpiperidin-4-yl) 2,2-diethylmalonate
8. poly- [6-[(1,1,3,3-tetramethylbutyl)-imino]-1,3,5-triazine-2,4-diyl][2-(1-acetoxy-2,2,6,6-tetramethylpiperidyl)-imino]-hexamethylene-[4-(1-acetoxy-2,2,6,6-tetramethylpiperidyl)-imino]
9. 1,4-diacetoxy-2,2,6,6-tetramethylpiperidine
10. 1-acetoxy-4-hydroxy-2,2,6,6-tetramethylpiperidine
11. di-(1-propionoxy-2,2,6,6-tetramethylpiperidin-4-yl) adipate
12. di-(4-benzoyloxy-2,2,6,6-tetramethylpiperidin-4-yl) oxalate
13. (1-acetoxy-2,2,6,6-tetramethylpiperidin-4-yl)-4-hydroxy-3,5-di-tert.butylbenzoate
14. 2-(4-hydroxy-3,5-di-tert.butylbenzyl)-2-(1-acetoxy-2,2,6,6-tetramethylpiperidin-4-yl) n-butylmalonate
15. N-(1-acetoxy-2,2,6,6-tetramethylpiperidin-4-yl)-N-(n-butyl) -4-(4-hydroxy-3,5-di-tert.butylbenzoyloxy)-3,5-di-tert.butylbenzamide
16. 1,6-di-(N-acetyl-N-(1-acetoxy-2,2,6,6-tetramethyl-piperidin-4-yl)]aminohexane
17. di-(1-acetoxy-2,2,6,6-tetramethylpiperidin-4-yloxy)-hexane-1,6-dicarbamate
18. 1-acetoxy-4-(N-acetyl-N-n-dodecylamino)-2,2,6,6-tetramethylpiperidine
19. di-(1-propionoxy-2,2,6,6-tetramethylpiperidin-4-yl) succinate
20. di-(4-n-octadecanoyloxy-2,2,6,6-tetramethyl-piperidin-1-yl)oxalate
21. 1,4-di-(2-ethylhexanoyloxy)-2,2,6,6-tetramethyl-piperidine
22. di-(1-benzoyloxy-2,2,6,6-tetramethylpiperidin-4-yl) sebacate
23. 1-benzoyloxy-4-(N-n-butyl-N-benzoylamino)-2,2,6,6-tetramethylpiperidine
24. 1-(1-benzoyloxy-2,2,6,6-tetramethylpiperdin-4-yl)-azepin-2-one
25 [1-benzoyloxy-1'-benzyloxy-di-(2,2,6,6-tetramethyl-piperidin-4-yl)]isophthalate
26 1,4-di-(4-hydroxy-3,5-di-tert-butylbenzoyloxy)-2,2,6,6-tetramethylpiperidine
27. n-butyl-(4-benzoyloxy-2,2,6,6-tetramethylpiperidin-4-yl)carbonate
28. 1-carbamoyloxy-4-benzoyloxy-2,2,6,6-tetramethyl-piperidine
29. di-(1-carbamoyloxy-2,2,6,6-tetramethylpiperidin4-yl)sebacate
30. di-(1-n-butylcarbamoyloxy-2,2,6,6-tetramethyl-piperidin-4-yl) 2,2-diethylmalonate
31. di-(4-benzoyloxy-2,2,6,6-tetramethylpiperidin-1-yl)-2,4,4-trimethylhexane-1,6-dicarbamate
32 1,4-dimethoxy-2,2,6,6-tetramethylpiperidine
33. 4-benzoyloxy-1-methoxy-2,2,6,6-tetramethylpiperidine
34. di-(1-methoxy-2,2,6,6-tetramethylpiperidin-4-yl) sebacate
35. alpha,alpha'-(di-1-ethoxy-2,2,6,6-tetramethylpiperidin-4-yloxy)-p-xylene
36. di-(1-benzoyloxy-2,2,6,6-tetramethylpiperidin-4-yl) phthalate
37. di-(1-benzyloxy-2,2,6,6-tetramethylpiperidin-4-yl)-diethylmalonate
38. poly-.[6-1,1,3,3-tetramethylbutyl)-imino]-1,2,5-triazine-2,4-diyl][2-(1-cyclohexyloxy-2,2,6,6-tetramethylpiperidyl)-imino]-hexamethylene-[4-(1-cyclohexyloxy-2,2,6,6-tetramethylpiperidyl)-imino]
39. (1-cyclohexyloxy-2,2,6,6-tetramethylpiperidin-4-yl)-3,5-di-t.butyl-4-hydroxybenzoate
40. 1-cyclohexyloxy-4-octadecanoyloxy-2,2,6,6-tetramethylpiperidine
41. di-(1-methoxy-2,2,6,6-tetramethylpiperidin-4-yl)succinate
42. di-(1-methoxy-2,2,6,6-tetramethylpiperidin-4-yl) isophthalate
43. di-(1-cyclohexyloxy-2,2,6,6-tetramethylpiperidin-4-yl)sebacate
44. di-(1-cyclohexyloxy-2,2,6,6-tetramethylpiperidin-4-yl)isophthalate
45. 4-benzoyloxy-1-(alpha-methylbenzyloxy)-2,2,6,6-tetramethylpiperdine
46. di-[1-(alpha-methylbenzyloxy)-2,2,6,6-tetramethyl-piperidin-4-yl]sebacate
47. di-(1-heptyloxy-2,2,6,6-tetramethylpiperidin-4-yl)sebacate
48. d-[1-(alpha-methylbenzyloxy)-2,2,6,6-tetramethyl-piperidin-4-yl]terephthalate
49. di-(1-ethoxy-2,2,6,6-tetramethylpiperidin-4-yl)sebacate
50. di-(1-cumyloxy-2,2,6,6-tetramethylpiperidin-4-yl)sebacate
51. 3,15-di-alpha-methylbenzyloxy-2,2,4,4,14,14,16,16-octamethyl-7,11,18,21-tetraoxa-3,15-diazatrispiro[5.2.2.5.2.2]heneicosane
52. 3,15-dicyclohexyloxy-2,2,4,4,14,14,16,16-octamethyl-7,11,18,21-tetraoxa-3,15-diazatrispiro[5.2.2.5.2.2]heneicosane
53. di-(1-cyclohexyloxy-2,2,6,6-tetramethylpiperidin4-yl)succinate
54. di-[1-alpha-methylbenzyloxy)-2,2,6,6-tetramethyl-piperidin-4-yl]succinate
55. di-(1-nonyloxy-2,2,6,6-tetramethylpiperidin-4-yl)sebacate
56. di-(1-octadecyloxy-2,2,6,6-tetramethylpiperidin-4-yl)sebacate
57. di-(1-nonyloxy-2,2,6,6-tetramethylpiperidin-4-yl)succinate
58. di-[1-(1-methylcyclohexyloxy)-2,2,6,6-tetramethyl-piperidin-4-yl]sebacate
59. di-[1-(3-cyclohexen-1-yloxy)-2,2,6,6-tetramethyl-piperidin-4-yl]sebacate 60. di-(1-tert.butoxy-2,2,6,6-tetramethylpiperidin-4-yl)sebacate
61. di-(1-carbamoyloxy-2,2,6,6-tetramethylpiperidin-4-yl)n-butylmalonate
62. di-[1-(bicyclo-[4.4.0]-decyl-1-oxy)-2,2,6,6-tetramethylpiperidin-4-yl]sebacate
63. di-(1-n-butylcarbamoyloxy-2,2,6,6-tetramethylpiperidin-4-yl)phthalate
64. di-(1-n-butylcarbamoyloxy-2,2,6,6-tetramethylpiperidin-4-yl)n-butylmalonate
65. di-(1-phenylcarbamoyloxy-2,2,6,6-tetramethylpiperidin-4-yl)sebacate
66. 4-benzoyloxy-1-benzyloxy-2,2,6,6-tetramethylpiperidine
67. di-(1-octyloxy-2,2,6,6-tetramethylpiperidine-4-yl)sebacate
68. di-(1-benzyloxy-2,2,6,6-tetramethylpiperidine-4-yl)sebacate
69 N,N',N'',N'''-tetrakis{2,4-bis[N-1-cyclohexyloxy2,2,6,6-tetramethylpiperidin-4-yl) n-butylamino]-1,3,5-triazin-6-yl -3,3'-ethylenediiminodipropylamine
70. 2,4,6-tris[N-6-cyclohexyloxy-2,2,6,6-tetramethylpiperidin-4-yl) -n-butylamino]-1,3,5-triazine
71. 2,4-bis[N-(1-cyclohexyloxy-2,2,6,6-tetramethylpiperidin-4-yl) -n-butylamino]-6-morpholino-1,3,5,-triazine
72. 1-octyloxy variation of compound 69
73. N,N'-bis(1-cyclohexyloxy-2,2,6,6-tetramethylpiperidin-4-yl) -N,N'-bis{2,4-bis[N-(1-cyclohexyloxy2,2,6,6-tetramethylpiperidin-4-yl) -n-butylamino]]-1,3,5-triazin-6-yl}hexamethylene diamine
74. N,N'-bis[2,4-bis[N-(1-cyclohexyloxy-2,2,6,6-tetramethylpiperidin-4-yl) -n-butylamino]-1,3,5-triazin-6-yl}piperazine
75. N-(1-cyclohexyloxy-2,2,6,6-tetramethylpiperidin-4-yl) succinimide
76. N-(1-methoxy-2,2,6,6-tetramethylpiperidin-4-yl) n-dodecyl succinimide
77. tetrakis(1-octyloxy-2,2,6,6-tetramethylpiperidin-4-yl)-1,2,3,4-butanetetracarboxylate
78. (1-methoxy-2,2,6,6-tetramethylpiperidin-4-yl)(1-octyloxy-2,2,6,6-tetramethylpiperidin-4-yl)sebacate.

The hydroxylamine derivatives of the instant invention are generally prepared by oxidizing the corresponding hindered amine with an appropriate peroxy compound such as hydrogen peroxide or tert-butyl hydroperoxide in the presence of a metal carbonyl or metal oxide catalyst followed by reduction of the oxyl intermediate formed to the desired N-hydroxy derivative, preferably by catalytic hydrogenation. Thereafter, the N-acyloxy derivatives are prepared by reacting the N-hydroxy hindered amine with the appropriate acid chloride, anhydride, isocyanate or substituted chloroformate. The catalytic hydrogenation can also be conducted in acetic anhydride to prepare the N-acetoxy derivative.

O-alkyl substituted N-hydroxy derivatives can be synthesized by several routes. The N-hydroxy derivative can be alkylated with sodium hydride and halogenated hydrocarbons such as benzyl bromide and ethyl iodide. N-methoxy variants can be prepared by thermolysis of a chlorobenzene solution of nitroxyl radical and di-tert-butyl peroxide. The product is formed by a coupling reaction between the nitroxyl radical and methyl radical generated from β-scission of a t-butoxy radical. Other N-alkoxy variants are synthesized by coupling nitroxyl radicals with hydrocarbon radicals generated from thermal decompostion of di-tert-butyl peroxide in the presence of hydrocarbon solvents such as cyclohexane, toluene, and ethylbenzene. Significant amounts of N-methoxy HALS are also formed in most of these reactions.

A preferred approach is the preparation of N-alkoxy hindered amines directly from hindered amines. For example, a mixture of 4-benzoyloxy-2,2,6,6-tetramethylpiperidine, aqueous t-butyl hydroperoxide, molybdenum oxide, and ethylbenzene gives a 90% yield of N-alpha-methylbenzyloxy HALS. Molybdenum (VI) has been shown to increase the efficiency of both the oxidation of hindered amine to nitroxyl radical and the reaction of nitroxyl radicals with hydrocarbons. In addition, the N-hydroxy derivatives can be reacted with potassium t-butoxide and methyl acrylate to synthesize the N-alkoxy variants possessing an ester functionality.

The oxalates of formula N can be prepared by reacting (1-hydroxy-2,2,6,6-tetramethylpiperidin-4-yl)stearate, benzoate, and the like, with oxalylchloride, or for G being —NH—G'—NH by reacting the appropriate 1-hydroxy2,2,6,6-tetramethyl piperidine with the appropriate diisocyanate.

The hindered amine precursors are large commercially available or can be prepared by methods known in the art.

The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1. Part 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

Although major emphasis in this application is directed to acid catalyzed baked finishes, it is also to be noted that the instant $NOR_1$ substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like. Correspondingly, the epoxide may be utilized as the crosslinking agent for various acrylic or polyester resin systems that have been modified by the presence of reactive groups on the backbone structure.

The amount of polyalkylpiperidine derivative employed is 0.1 to 5% by weight, based on the solvent-free binder, preferably 0.5 to 2% by weight. The binders can be dissolved or dispersed in customary organic solvents or in water or can be solvent-free.

When used in two-coat finishes, the polyalkylpiperidine derivative can be incorporated in the clear coat or both in the clear coat and in the pigmented base coat.

To attain maximum light stability, the concurrent use of other conventional light stabilizers can be advantageous. Examples are UV absorbers of the benzophenone, benzotriazole, acrylic acid derivative, or oxalanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of the UV absorbers which may be used in the instant compositions in conjunction with the aforementioned piperidine compounds are:

(a) 2-(2'-Hydroxyphenyl)-benzotriazoles, for example, the 5'-methyl-, 3', 5'-di-tert-butyl-, 5'-tert-butyl-, 5'-(1,1,3,3-tetramethylbutyl)-, 5-chloro-3', 5'-di-tert-butyl-, 5-chloro-3'-tert-butyl-5'-methyl-, 3'-sec-butyl-5'-tert-butyl-, 4'-octoxy-, 3', 5'-di-tert-amyl derivative.

(b) 2-Hydroxy-benzophenones, for example, the 4-hydroxy-, 4-methoxy-, 4-oxtoxy-, 4-decyloxy-, 4-dodecyloxy-, 4-benzyloxy, 4,2', 4'-trihydroxy- and 2'-hydroxy-4,4'-dimethoxy derivative.

(c) Acrylates, for example, alpha-cyano-$\beta,\beta$-diphenylacrylic acid ethyl ester or isoctyl ester, alphacarbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyl-oxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylamino-propyl)-oxalamide, 2-ethoxy-5-tert-butyl-2'-ethyl-oxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl) 4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy3,5-di-tert-octylphenyl) -2H-benzotriazole, 2-(2-hydroxy3-alpha,alpha-dimethylbenzyl -5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tertbutyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert.butyl5-(2-octyloxycarbonyl) ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alphadimethyl-benzyl)phenyl]-2H-benzotriazole, dodecylated 2-(2-hydroxy-5-methylphenyl) -2H-benzotriazole, 2-[2-hydroxy-3-tert-butyl -5-(2-(omega-hydroxy-octa-(ethyleneoxy) carbonyl)-ethylphenyl]-2H-benzotriazole, 2-[2-hydroxy-3-tert.butyl-5-(2-octyloxycarbonyl)ethylphenyl]-2H-benzotriazole and 5-chloro-2-[2-hydroxy-3-tert.butyl-5-(2-octyloxycarbonyl)ethylphenyl]-2H-benzotriazole.

A preferred embodiment of the instant invention pertains to stabilized compositions comprising
(a) an acid catalyzed thermoset coating or enamel based on hot crosslinkable acrylic, polyester or resins,
(b) a $NOR_1$-substituted 2,2,6,6-tetraalkylpiperidine compound, and
(c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

The following examples describe the inventive use of the substituted polyalkylpiperidine derivatives in acid catalyzed stoving lacquers based on acrylic resin containing binder systems. Parts and percentages are by weight.

EXAMPLE 1

Stabilization of High Solids Acid-catalyzed, Thermoset Acrylic Resin Enamel

A high solids (50% by weight) thermoset acrylic resin enamel, catalyzed by 0.5% by weight of p-toluenesulfonic acid, based on the film-forming resin, is stabilized by the addition of various derivatives of the instant invention. The high solids thermoset acrylic resin enamel formulation (Acryloid AT 400 from Rohm and Haas) is based on hydroxyethyl methacrylate, methyl methacrylate, styrene, butyl acrylate and butyl methacrylate and a melamine curing agent.

Pieces of steel sheeting 4"×12"(9.16 cm×30.48 cm), coated with a primer based on polyester/epoxy resin, are then coated with a $TiO_2$-pigmented base coat based on a binder of 70% of monomers such as hydroxyethyl acrylate, styrene, acrylonitrile, butyl acrylate and acrylic acid with 30% of a melamine resin and an acid catalyst and finally with the clear finishing enamel. The base coat is sprayed onto the sheet to a thickness of about 0.8 mil (0.0203 mm), air dried for 3 minutes and baked at 121° C. for 10 minutes. The clear finishing enamel coat is then wire-coated onto the sheet to a thickness of about 2.5 mil. After 15 minutes air-drying, the coated sheets are baked for 30 minutes at 82° C.

The stabilizers under test are added to the thermoset acrylic resin finishing enamel in concentrations of 2% by weight, before the enamel is coated onto the base coated sheet.

Gardner yellowness index color values are determined on the baked sample and on the sample after having been subjected to an additional 30 minutes baking at 82° C.

In addition, after storage for 3 weeks in an air-conditioned room (23° C./50% relative humidity), the coated sheets are subjected to weathering for 150 hours according to test method ASTM G-53/77 in a QUV exposure apparatus. In this apparatus, the samples are subjected to weathering in repeated cycles for 4 hours in a humid atmosphere at 50° C. and then for 8 hours under UV light at 70° C. Equivalent samples are also subjected to accelerated weathering for 2625 hours in a Xenon arc (6500 watt) Weather-ometer. The samples are exposed to repeated cycles for 102 minutes to the light source, then for 18 minutes to a water spray and light at 60° C. The Gardner color value is also determined for each sample after QUV and Xenon exposure.

| | | Color Change | | |
|---|---|---|---|---|
| Compound | Orig. Color | Overbake | QUV | Xenon |
| Unstabilized | 1.0 | 0.8 | 23.0 | 24.5 |
| 3 | 1.2 | 0.8 | 13.1 | 3.9 |
| 9 | 1.2 | 0.6 | 15.0 | 4.6 |
| 26 | 3.3 | 0.8 | 12.4 | 1.8 |
| 28 | 1.0 | 0.3 | 15.3 | 3.8 |

These data illustrate the effective stabilization characteristics of the coatings of the invention, such performance being particularly evident under the extreme weather conditions.

EXAMPLE 2

The samples of Example 1 are also evaluated on the basis of Knoop Hardness (ASTM D-1474-68) on the baked and overbaked samples; distinction of image (DOI), Hunter Associates Apparatus; 20° gloss (ASTM D-523-80); and cracking based on visual observation on a scale of 0–8 with "0" reflecting absence of cracking and "8" reflecting excessive cracking and "a", "b", "c" designations for crack depth with "a" reflecting shallow cracks and "c" reflecting deepest cracks.

| | Knoop Hardness | | QUV Exposure | | | | | | | | Xenon |
|---|---|---|---|---|---|---|---|---|---|---|---|
| | | | 20° Gloss | | | DOI | | | Cracks | | |
| Compound | Bake | Overbake | 575 hrs. | 750 | 900 | 575 | 750 | 900 | 750 | 900 | Time to Crack (hrs.) |
| Unstabilized | 5.5 | 8.0 | 13 | 11 | — | 9 | 4 | — | 8c | — | <<2300 (8c) |
| 3 | 5.5 | 8.0 | 84 | 70 | 29 | 90 | 85 | 12 | 0 | 3a | 2900 |
| 9 | 5.5 | 8.0 | 85 | 56 | 12 | 90 | 62 | 7 | 5a | 6a | <2300 (6b) |
| 26 | 5.5 | 8.0 | 85 | 44 | 8 | 92 | 51 | 12 | 7a | 7a | 3000 |
| 28 | 4.0 | 6.5 | 90 | 66 | 17 | 95 | 77 | 3 | 0 | 7a | 2625 |

These data illustrate a pattern of greater retention of gloss and DOI and longer absence of severe cracking after the indicated exposure conditions.

EXAMPLE 3

The thermoset acrylic enamel of Example 1 is formulated to include 2% by weight of a benzotriazole UV-absorber and 1.5%, by weight, of the hindered amine light stabilizer. The enamel is coated over a white base coat or over a silver metallic base coat. Baking is conducted for 30 minutes at either 121° C. normal bake temperature or at 82° C. automotive low bake repair temperature.

The coated panels are exposed in the QUV exposure apparatus and 20° gloss and distinction of image (DOI) values are determined.

A. 121° C. Bake Temp. with white base coat

| Compound | Hours of QUV Exposure | | | | | |
|---|---|---|---|---|---|---|
| | 20° Gloss | | | DOI | | |
| | 0 | 1421 | 2106 | 0 | 1421 | 2106 |
| Unstabilized | 93 | (655 hrs)* | — | 88 | (655 hrs)* | — |
| Compound A | 94 | 9 | 3* | 89 | 15 | 3* |
| A + 3 | 93 | 64 | 16* | 89 | 81 | 47* |
| A + 10 | 93 | 102 | 90* | 84 | 82 | 59* |
| A + 13 | 93 | 33** | — | 87 | (655 hrs)* | — |
| A + 14 | 90 | 23 | 3* | 86 | 2 | 0* |
| A + 16 | 93 | 92 | 62* | 88 | 81 | 58* |
| A + 17 | 92 | 67 | 12* | 91 | 85 | 45* |
| A + 18 | 94 | 55 | 7* | 89 | 80 | 21* |
| A + 21 | 92 | 69* | — | 82 | 57* | — |

*cracking observed
**gloss value at 655 hours
Compound A — 2-[2'-hydroxy-3',5'-di-(alpha,alpha-dimethylbenzyl)phenyl]benzotriazole B. 121° C. Bake Temp. with silver metallic base coat

| Compound | Hours of QUV Exposure | | | | | | | | | |
|---|---|---|---|---|---|---|---|---|---|---|
| | 20° Gloss | | | | | DOI | | | | |
| | 0 | 674 | 916 | 1118 | 1377 | 0 | 674 | 916 | 1118 | 1377 |
| Unstabilized | 92 | 2* | — | — | — | 87 | 2 | — | — | — |
| Compound A | 90 | 51 | 5 | 3 | 2.2* | 84 | 65 | 6 | 5 | −2.5 |
| A + 3 | 95 | 86 | 53 | 18 | 4.8* | 88 | 79 | 78 | 48 | 28 |
| A + 10 | 94 | 85 | 44 | 22* | — | 88 | 78 | 48 | 13 | — |
| A + 13 | 92 | ** | — | — | — | 86 | — | — | — | — |
| A + 14 | 92 | 86 | 93 | 26* | — | 89 | 86 | 75 | 26 | — |
| A + 16 | 92 | 93 | 72 | 32* | — | 90 | 88 | 75 | 28 | — |
| A + 17 | 93 | 82 | 60 | 33 | 8* | 85 | 83 | 80 | 59 | 29 |
| A + 18 | 93 | 85 | 40 | 9 | 3* | 89 | 86 | 67 | 44 | 20 |
| A + 21 | 91 | 89 | 64 | 29* | — | 71 | 68 | 54 | 28 | — |

**gloss value at 460 hours.

EXAMPLE 4

Two thermoset acrylic enamels are formulated to include 2%, by weight, of a benzotriazole UV-absorber and 1%, by weight of a hindered amine light stabilizer as described in Example 3.

The thermoset acrylic enamels are based on a binder of 70% of monomers such as hydroxyethyl acrylate, styrene, acrylonitrile, butyl acrylate and acrylic acid with 30% of a melamine resin and an acid catalyst, such as p-toluene-sulfonic acid, dinonylnaphthalenedisulfonic acid, dodecylbenzenesulfonic acid or phenyl acid phosphate.

Pieces of steel sheeting 4"×12" (9.16 cm×30.48 cm), coated with a primer based on polyester/epoxy resin, are then coated with the white base coat and finally with the clear finishing enamel. The base coat is sprayed onto the sheet to a thickness of about 0.8 mil (0.0203 mm) and air dried for 3 minutes. The clear finishing enamel coat is then sprayed onto the sheet to a thickness of about 1.5 mil (0.0381 mm). After 15 minutes air-drying, the coated sheets are baked for 30 minutes at 121° C. QUV evaluations are then conducted.

| Compound | Test | Hours of QUV Exposure | | | | | |
|---|---|---|---|---|---|---|---|
| | | 0 | 1010 | 1270 | 1594 | 1826 | 2036 |
| Unstabilized | 20° Gloss | 89 | 25 | 23* | — | — | — |
| | DOI | 92 | 5 | 4 | — | — | — |
| A + 14 | 20° Gloss | 91 | 91 | 89 | 82 | 48 | 34* |
| | DOI | 98 | 90 | 86 | 87 | 47 | 45 |

EXAMPLE 5

A white polyester/melamine based oil-free alkyd coil coating is utilized in this example. The fully formulated paint is applied over a primed steel sheet using a wire wound rod to give a 0.6–0.8 mil dry film. The panels are baked for about 90 seconds at 220° C., removed from oven and immediately quenched in water. The coated panels are exposed in a Carbon Arc Weatherometer, a Xenon Arc Weatherometer, and in South Florida at an angle of 45° S to the sun. 20° gloss values are determined.

| | Exposure Time | Unstabilized | 2%, by wt. Compound 9 |
|---|---|---|---|
| Carbon Arc Weatherometer | 0 (Hrs.) | 78 | 81 |
| | 112 | 69 | 78 |
| | 262 | 15 | 45 |
| | 337 | 11 | 37 |
| | 447 | 14 | 31 |
| Xenon Arc Weatherometer | 0 (Hrs.) | 78 | 81 |
| | 150 | 75 | 83 |
| | 378 | 63 | 75 |
| | 709 | 11 | 23 |
| | 954 | 5 | 12 |
| Florida 45° S Direct Weather | 0 (Mos.) | 78 | 81 |
| | 6 | 76 | 79 |
| | 12 | 39 | 60 |

EXAMPLE 6

The thermoset acrylic enamel of Example 4 including 0.5% of p-toluenesulfonic acid is formulated to include varying concentrations of a benzotriazole UV-absorber and a hindered amine light stabilizer of the invention. The enamel is coated over a silver metallic base coat pursuant to the procedure in Example 4 and baking in conducted for 30 minutes at 121° C. normal bake temperature.

The coated panels are exposed in the QUV exposure apparatus and the time to 50% loss of 20° gloss is determined.

| Compound | Conc. (%, by wt.) | Time to 50% loss of 20° Gloss (hours) |
|---|---|---|
| unstabilized | — | 700 |
| B | 3.5 | 1400 |
| B/22 | 3.5/1.5 | 2100 |
| B/45 | 3.5/1.5 | 2050 |
| B/66 | 3.5/1.5 | 2150 |
| unstabilized | — | 900 |
| B/C | 3.5/0.25* | 3000 |
| B/1 | 3.5/1.5 | 3600 |
| B/2 | 3.5/1.5 | 4200 |

-continued

| Compound | Conc. (% by wt.) | Time to 50% loss of 20° Gloss (hours) |
|---|---|---|
| B/23 | 3.5/1.5 | 3200 |
| B/26 | 3.5/1.5 | 3700 |
| B/32 | 3.5/1.5 | 3900 |
| B/33 | 3.5/1.5 | 4200 |
| B/35 | 3.5/1.5 | 4800 |
| unstabilized | — | 1000 |
| B/1 | 3/1 | 3800 |
| B/2 | 3/1 | 3400 |
| B/4 | 3/1 | 3950 |
| B/19 | 3/1 | 4000 |
| B/22 | 3/1 | 3700 |
| B/25 | 3/1 | 3700 |
| B/26 | 3/1 | 3700 |
| B/34 | 3/1 | 4000 |
| B/36 | 3/1 | 4100 |
| B/42 | 3/1 | 4100 |
| B/43 | 3/1 | 4100 |
| B/44 | 3/1 | 4300 |
| B/45 | 3/1 | 3900 |
| B/46 | 3/1 | 4800 |
| B/47 | 3/1 | 4300 |
| B/48 | 3/1 | 3800 |
| B/66 | 3/1 | 3700 |

Compound B — 2-[2-hydroxy-3-tert.butyl-5-(2-(omega-hydroxy-octa(ethyleneoxy)-carbonyl)-ethylphenyl]-2H-benzotriazole
Compound C — di-(1,2,2,6,6-pentamethylpiperidin-4-yl)-sebacate
*low concentration required due to cure retardation at higher levels

EXAMPLE 7

A thermoset acrylic enamel based on a binder of 70% of monomers such as hydroxyethyl acrylate, butyl acrylate, butylemethacrylate, styrene and acrylic acid with 30% of a melamine resin and an acid catalyst such as p-toluenesulfonic acid, dinonylnaphthalene disulfonic acid or dodecylbenzene sulfonic acid is formulated. Commercially available 9.16 cm×30.48 cm Uniprime panels are used as the substrate. They are coated with a silver metallic basecoat and then with the clear finishing enamel. The basecoat is stabilized with 1% Compound B and 1% Compound D (based on solid resin) and is sprayed onto the panel to a thickness of about 0.6–0.8 mil and air dried for 3 minutes. The clearcoat including the noted stabilizers is then sprayed to a thickness of 1.7–2.0 mils and after 10 minutes of air-drying, the coated panels are baked for 30 minutes at 121° C. The coated panels are exposed in a QUV exposure apparatus and distinction of image (DOI) values are determined.

| Compound | Conc. (% by wt.) | DOI After QUV Exosure | | | | |
|---|---|---|---|---|---|---|
| | | 0 | 609 | 1252 | 2164 | 3391 Hours |
| Unstabilized* | — | 85 | 21 | 13** | | |
| B/D | 3/1.5 | 83 | 87 | 83 | 84 | 52 |
| B/48 | 3/1.5 | 82 | 83 | 85 | 84 | 72 |
| B/67 | 3/1.5 | 81 | 83 | 85 | 82 | 72 |

*No stabilizer in either basecoat or clearcoat
**Indicates cracking
Compound D — 8-acetyl-3-dodecyl-7,7,9,9-tetramethyl-1,3,8-triazaspiro(4,5)-decane-2,4-dione

EXAMPLE 8

A waterborne acrylic melamine enamel is formulated as shown below.

| | Parts Resin Solids |
|---|---|
| Synthacryl VSW 6483 (acrylic dispersion from Hoechst AG) | 30 |
| Synthacryl VSW 6484 (50% acrylic resin in butyl diglycol) | 42 |
| Maprenal MF 915 (70% melamine resin in isobutyl alcohol) | 25 |
| Maprenal MF 927 (melamine resin) | 3 |
| | 100 |

A water-based basecoat/clearcoat enamel is prepared by spray applying a 0.6–0.8 mil thick film of commercial silver metallic waterborne basecoat (from BASF AG) over an epoxy primed coil coated aluminum panel. This material is baked at 80° C. for 5 minutes and then clearcoated with 1.6–1.8 mil of the waterborne enamel. The system is baked at 80° C. for 10 minutes and then at 140° C. for a further 30 minutes. Prior to application of the clearcoating, light stabilizers dissolved in a minimum amount of butyglycol acetate are added to the paint. The coated panels are exposed in the QUV for 975 hours. The distinctness of image (DOI) retention of the panels after exposure is reported.

| Compound | Conc. (% by wt.) | % DOI Retention |
|---|---|---|
| — | — | 21 |
| C | 1 | 24 |
| 48 | 1 | 55 |
| 67 | 1 | 38 |

EXAMPLE 9

An acrylic ketimine basecoat/clearcoat system is stabilized in the clearcoat with the indicated amount of ultraviolet light absorber and hindered amine derivative. The basecoat is spray applied to a thickness of 0.8 mil onto a ketimine-acetoacetate primed cold rolled steel panel. It is clearcoated with 2.4 mil of an unsaturated acrylate-ketimine enamel (wet on wet). The panels are baked for 45 minutes at 60° C. and are then exposed in a QUV exposure apparatus. In this apparatus, the samples are subjected to weathering in repeated cycles for 4 hours in a humid atmosphere at 50° C. and then for 4 hours under UV light at 60° C. The 20° gloss of the panels are reported at different exposure intervals.

| Compound | Conc. (% by wt.) | 20° Gloss Hours of QUV Exposure | | | | | |
|---|---|---|---|---|---|---|---|
| | | 0 | 400 | 800 | 1200 | 1600 | 2000 |
| — | — | 94 | 93 | 87 | 30* | | |
| B/48 | 1.5/1 | 94 | 93 | 89 | 56 | 31 | 34* |

*Indicates Cracking

EXAMPLE 10

A polyester-melamine coil coating catalyzed with p-toluenesulfonic acid is formulated to include a benzotriazole UV absorber and a hindered amine light stabilizer of the invention. The material is applied using a wire-wound rod and an automatic drawdown apparatus onto coil primed panels to a dry thickness of 0.8 mil. The panels are baked in a 260° C. oven for 45 seconds at which time the peak metal temperature is 225° C. Two colored systems, a phthalo blue and a bronze oxide pigmented system, are tested. The panels are exposed in South Florida at an angle of 45° S to the sun for 17 months. The color change (ΔE) of the panels are reported.

| Compound | Conc. (% by wt.) | |
|---|---|---|
| | | ΔE of brown panels |
| — | — | 6.7 |
| B/14 | 3/3 | 4.9 |
| B/68 | 3/3 | 4.7 |
| | | ΔE of Blue |
| — | — | 7.0 |
| B/46 | 3/3 | 5.3 |

EXAMPLE 11

The thermoset acrylic enamel of Example 7 is formulated to include a hindered amine light stabilizer of the invention. Coil coated aluminum panels primed with an epoxy primer are coated with 0.6-0.8 mil of a silver metallic basecoat and finally with 1.6-1.8 mil of the clear finishing enamel. After 5-10 minutes of air drying, the coated panels are baked for 30 minutes at 30° C.

The coated panels are exposed in the QUV exposure apparatus and the 20° gloss of the samples are determined at various intervals.

| Compound | Conc. (% by wt.) | 20° Gloss (after hours) | | | | | |
|---|---|---|---|---|---|---|---|
| | | 0 | 800 | 1600 | 2000 | 2400 | 2800 |
| — | — | 92 | 69 | 45* | | | |
| 3 | 1 | 91 | 83 | 72 | 61 | 50 | 36 |
| 22 | 1 | 91 | 88 | 76 | 46 | 42 | 16 |
| 68 | 1 | 92 | 84 | 64 | 53 | 48 | 14 |
| 48 | 1 | 92 | 79 | 49 | 49 | 43 | 20 |
| 43 | 1 | 92 | 90 | 79 | 73 | 63 | 31 |

*Indicates cracking

The data in these examples clearly illustrate the beneficial performance characteristics of the composition of this invention.

What is claimed is:

1. A stabilized stoving lacquer composition comprising (a) an acid catalyzed thermoset resin based on hot crosslinkable acrylic, polyester, polyurethane, polyamide or alkyd resins, and (b) an effective oxidative and light stabilizing amount of a hindered amine derivative corresponding to the formulae A-P

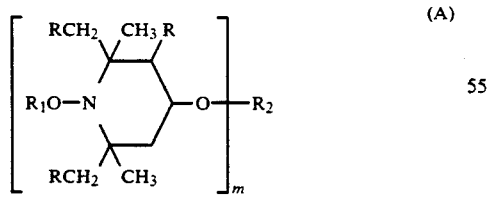
(A)

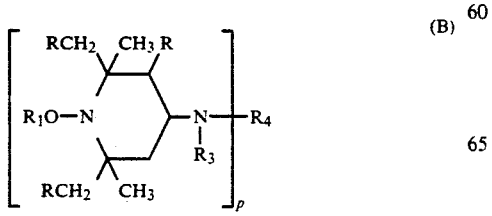
(B)

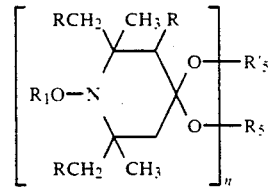
(C)

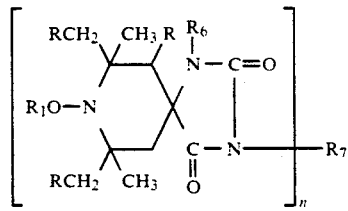
(D)

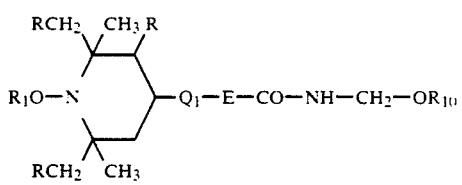
(E)

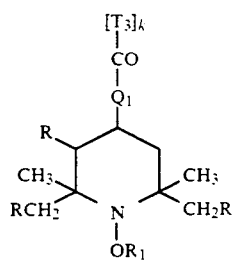
(F)

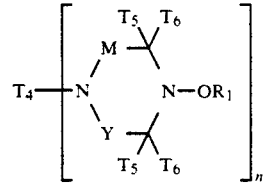
(G)

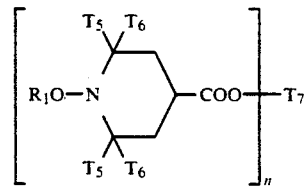
(H)

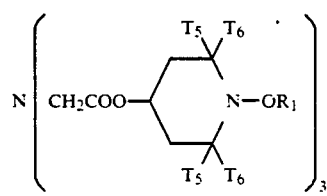
(I)

-continued

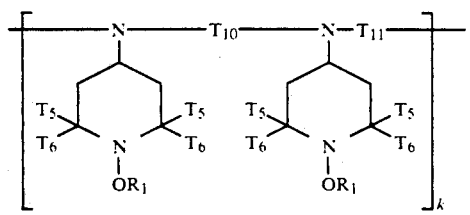 (J)

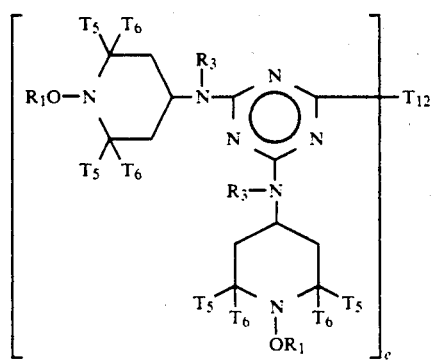 (K)

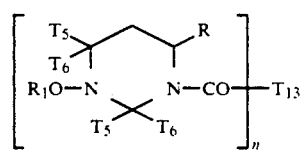 (L)

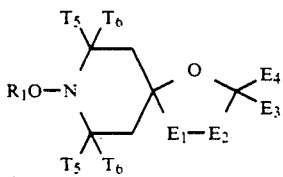 (M)

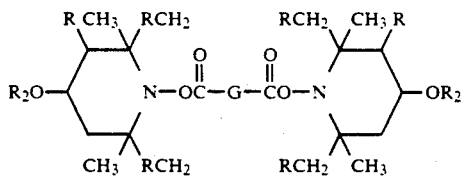 (N)

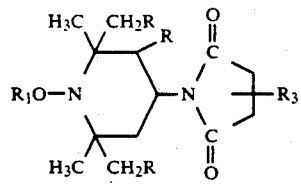 (O)

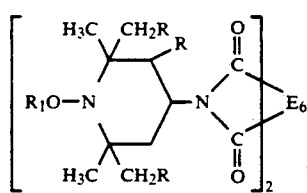 (P)

wherein
R is hydrogen or methyl,
$R_1$ is independently $C_1-C_{18}$ alkyl, $C_2-C_{18}$ alkenyl, $C_2-C_{18}$ alkynyl, $C_5-C_{12}$ cycloalkyl, $C_6-C_{10}$ bicycloalkyl, $C_5-C_8$ cycloalkenyl $C_6-C_{10}$ aryl, $C_7-C_9$ aralkyl, $C_7-C_9$ aralkyl substituted by alkyl or aryl, or

wherein D is $C_1-C_{18}$ alkyl, $C_1-C_{18}$ alkoxy, phenyl, phenyl substituted by hydroxy, alkyl or alkoxy, or amino or amino mono- or disubstituted by alkyl or phenyl;
m is 1-4,
when m is 1,
$R_2$ is hydrogen, $C_1-C_{18}$ alkyl optionally interrupted by one or more oxygen atoms, $C_2-C_{12}$ alkenyl, $C_6-C_{10}$ aryl, $C_7-C_{18}$ aralkyl glycidyl, a monovalent acyl radical of an aliphatic, cycloaliphatic, araliphatic or aromatic carboxylic acid, or of a carbamic acid, or

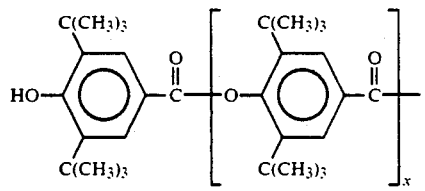

wherein x is 0 or 1, or

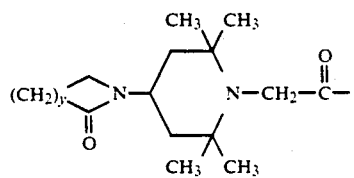

wherein y is 2-4;
when m is 2,
$R_2$ is $C_1-C_{12}$ alkylene, $C_4-C_{12}$ alkenylene, xylylene, a divalent acyl radical of an aliphatic, cycloaliphatic, araliphatic or aromatic dicarboxylic acid or of a dicarbamic acid;
when m is 3, $R_2$ is a trivalent acyl radical of an aliphatic, unsaturated aliphatic, cycloaliphatic, or aromatic tricarboxylic acid;
when m is 4, $R_2$ is a tetravalent acyl radical of a saturated or unsaturated aliphatic or aromatic tetracarboxylic acid;
p is 1 2 or 3,
$R_3$ is hydrogen, $C_1-C_{12}$ alkyl, $C_5-C_7$ cycloalkyl, $C_7-C_9$ aralkyl, $C_2-C_{18}$ alkanoyl, $C_3-C_5$ alkenoyl or benzoyl;
when p is 1,
$R_4$ is hydrogen, $C_1-C_{18}$ alkyl, $C_5-C_7$ cycloalkyl, $C_2-C_8$ alkenyl unsubstituted or substituted by a cyano, carbonyl or carbamide group, aryl, aralkyl, or it is glycidyl, a group of the formula —CH$_2$—CH(OH)—Z or of the formula —CO—Z or —CONH—Z wherein Z is hydrogen, methyl or phenyl; or a group of the formulae

[Structure: 2,2,6,6-tetramethylpiperidine ring with N—OR₁, substituents RCH₂, CH₂R at 2,6-positions and CH₃ groups]

[Structure: phenolic polymer]

$$HO-\underset{\underset{C(CH_3)_3}{|}}{\overset{\overset{C(CH_3)_3}{|}}{\bigcirc}}-\overset{O}{\overset{\|}{C}}-\left[O-\underset{\underset{C(CH_3)_3}{|}}{\overset{\overset{C(CH_3)_3}{|}}{\bigcirc}}-\overset{O}{\overset{\|}{C}}-\right]_h$$

with h as 0 or 1;

or $R_3$ and $R_4$ together when p is 1 can be alkylene of 4 to 65 carbon atoms or 2-oxopolyalkylene or the cyclic acyl radical of an aliphatic or aromatic 1,2- or 1,3-dicarboxylic acid, when p is 2, $R_4$ is a direct bond or is $C_1$-$C_{12}$ alkylene, $C_6$-$C_{12}$ arylene, xylylene, a —$CH_2CH(OH)$—$CH_2$ group, or a group —$CH_2$—$CH(OH)$—$CH_2$—O—X—O—$CH_2$—$CH(OH)$—$CH_2$— wherein X is $C_2$-$C_{10}$ alkylene, $C_6$-$C_{15}$ arylene or Chd $6$-$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—; or $R_4$ is

[Structure: triazine ring with N substituents T₈, T₉ via N]

where $T_8$ and $T_9$ are independently hydrogen, alkyl of 1 to 18 carbon atoms, or $T_8$ and $T_9$ together are alkylene of 4 to 6 carbon atoms or 3-oxapentamethylene;

when p is 3, $R_4$ is 2,4,6-triazinyl, n is 1 or 2, when n is 1, $R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or hydroxylakylene or $C_4$-$C_{22}$ acyloxyalkylene;

when n is 2, $R_5$ and $R'_5$ together are (—$CH_2$)$_2C$($CH_2$—)$_3$;

$R_6$ is hydrogen, $C_1$-$C_{12}$ alkyl, allyl, benzyl, glycidyl or $C_2$-$C_6$ alkoxyalkyl;

when n is 1, $R_7$ is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula —($CH_2$)$_t$—COO—Q or of the formula —($CH_2$)$_t$—O—CO—Q wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group —$CH_2CH(OH)$—$CH_2O$—X—O—$CH_2$—$CH(OH)$—$CH_2$— wherein X is $C_2$-$C_{10}$ alkylene, $C_6$-$C_{15}$ arylene or $C_6$-$C_{12}$ cycloalkylene, or a group —$CH_2CHY(OZ')CH_2$—($OCH_2$—$CH(OZ')CH_2$—)$_2$— wherein Z' is hydrogen, $C_1$-$C_{18}$ alkyl, allyl, benzyl, $C_2$-$C_{12}$ alkanoyl or benzoyl;

$Q_1$ is —$N(R_8)$— or —O—;

E is $C_1$-$C_3$ alkylene, the group —$CH_2$—$CH(R_9)$—O— wherein $R_9$ is hydrogen, methyl or phenyl, the group —($CH_2$)$_3$—NH— or a direct bond;

$R_{10}$ is hydrogen or $C_1$-$C_{18}$ alkyl;

$R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —$CH_2$—$CH(R_9)$—OH wherein $R_9$ has the meaning defined above; a group of the formula

[Structure: piperidine ring with R₁O—N, RCH₂, CH₃ substituents]

or a group of the formula $$-G_1-N-E-CO-NH-CH_2-OR_2$$

[Structure: piperidine ring with OR₁ on N, H₃C, CH₃, RH₂C, CH₂R substituents]

wherein $G_1$ can be $C_2$-$C_6$ alkylene or $C_6$-$C_{12}$ arylene; or $R_8$ is a group —E—CO—NH—$CH_2$—$OR_{10}$;

$T_3$ is ethylene or 1,2-propylene, or is the repeating structural unit derived from an alpha-olefin copolymer with an alkyl acrylate or methacrylate;

k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene;

M and Y are independently methylene or carbonyl;

$T_7$ is the same as $R_7$;

$T_{10}$ and $T_{11}$ are independently alkylene of 2 to 12 carbon atoms, or $T_{11}$ is

[Structure: triazine ring with T₈, T₉ substituents via N]

$T_{12}$ is piperazinyl, $$-NR_{11}-(CH_2)_d-NR_{11}-\quad\text{or}$$

$$-NH(CH_2)_a-\overset{|}{N}(CH_2)_b-\overset{|}{N}[(CH_2)_c-\overset{|}{N}]_fH$$

wherein
$R_{11}$ is the same as $R_3$ or is also

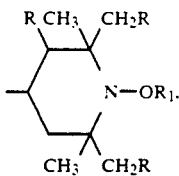

a, b and c are independently 2 or 3, and f is 0 or 1;
e is 2, 3 or 4;
$T_{13}$ is the same as $R_2$ with the proviso that $T_{13}$ cannot be hydrogen when n is 1;
$E_1$ and $E_2$, being different, each are —CO— or —N-($E_5$)— wherein $E_5$ is hydrogen, $C_1$-$C_{12}$ alkyl or $C_4$-$C_{22}$ alkoxycarbonylalkyl;
$E_3$ is hydrogen, alkyl of 1 to 30 carbon atoms, phenyl, naphtyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms;
$E_4$ is hydrogen, alkyl of 1 to 30 carbon atoms, phenyl, naphtyl or phenylalkyl of 7 to 12 carbon atoms, or
$E_3$ and $E_4$ together are polymethylene of 4 to 17 carbon atoms, or said polymethylene substituted by up to four alkyl groups of 1 to 4 carbon atoms;
$R_2$ of formula (N) is a previously defined when m is 1;
G is a direct bond, $C_1$-$C_{12}$ alkylene, phenylene or —NH—G'-NH wherein G' is $C_1$-$C_{12}$ alkylene; and
$E_6$ is an aliphatic or aromatic tetravalent radical.

2. A composition according to claim 1 wherein the compound of component (b) is selected from the group consisting of
di-(1-acetoxy-2,2,6,6-tetramethylpiperdin-4-yl)phthalate,
di-(1-acetoxy-2,2,6,6-tetramethylpiperdin-4-yl)phthalate,
di-(1-acetoxy-2,2,6,6-tetramethylpiperdin-4-yl) sebacate,di-(1-acetoxy-2,2,6,6-tetramethylpiperdin-4-yl)succinate,di-(1-acetoxy-2,2,6,6-tetramethylpiperidin-4-yl) adipate
di-(1-acetoxy-2,2,6,6-tetramethylpiperdin-4-yl) n-butylmalonate,
di-(1-acetoxy-2,2,6,6-tetramethylpiperdin-4-yl) 2,2-diethylmalonate,
poly- [6-[(1,1,3,3-tetramethylbutyl)-imino]-1,3,5-triazine-2,4-diyl][2-(1-acetoxy-2,2,6,6-tetramethylpiperidyl) -imino]-hexamethylene-[4-(1-acetoxy-2,2,6,6-tetramethyl piperidyl)-imino],
1,4-diacetoxy-2,2,6,6-tetramethylpiperdine,
1-acetoxy-4-hydroxy-2,2,6,6-tetramethylpiperidine, (1-acetoxy-2,2,6,6-tetramethylpiperdin-4-yl)-4-hydroxy-3,5-di-tert.butylbenzoate,
2-(4-hydroxy-3,5-di-tert.butylbenzyl)-2-(1-acetoxy-2,2,6,6-tetramethylpiperidin-4-yl) n-butylamalonate,
N-(1-acetoxy-2,2,6,6-tetramethylpiperdin-4-yl)-N-(n-butyl)-4-(4-hydroxy-3,5-di-tert.butylbenzoyloxy) -3,5-di-tert.butylbenzamide,
1,6-di-(N-acetyl-N-(1-acetoxy-2,2,6,6-tetramethylpiperidin-4-yl)]aminohexane,
di-(1-acetoxy-2,2,6,6-tetramethylpiperidin-4-yloxy)-hexane-1,6-dicarbamate,
1-acetoxy-4-(N-acetyl-N-n-dodecylamino)-2,2,6,6-tetramethylpiperidine,
di-(1-propionoxy-2,2,6,6-tetramethylpiperdin-4-yl) succinate,
di-(4-n-octadecanoyloxy-2,2,6,6-tetramethylpiperidin-1-yl)oxalate,
1,4-di-(2-ethylhexanoyloxy)-2,2,6,6-tetramethylpiperidine,
di-(1-benzoyloxy-2,2,6,6-tetramethylpiperidin-4-yl) sebacate,
1-benzoyloxy-4-(N-n-butyl-N-benzoylamino)-2,2,6,6-tetramethylpiperidine,
1-(1-benzoyloxy-2,2,6,6-tetramethylpiperdin-4-yl)azepin-2-one,
[1-benzoyloxy-1'-benzyloxy-di-(2,2,6,6-tetramethylpiperdin-4-yl)]isophthalate,
1,4-di-(4-hydroxy-3,5-di-tert-butylbenzoyloxy)-2,2,6,6-tetramethylpiperidine,
n-butyl-(4-benzoyloxy-2,2,6,6-tetramethylpiperidin-4-yl)carbonate,
1-carbamoyloxy-4-benzoyloxy-2,2,6,6-tetramethylpiperidine,
di-(1-carbamoyloxy-2,2,6,6-tetramethylpiperidin-4-yl)sebacate,
di-(1-n-butylcarbamoyloxy-2,2,6,6-tetramethylpiperidin-4-yl) 2,2-diethylmalonate,
di-(4-benzoyloxy-2,2,6,6-tetramethylpiperidin-1-yl)-2,4,4-trimethylhexane-1,6-dicarbamate,
1,4-dimethoxy-2,2,6,6-tetramethylpiperidine,
4-benzoyloxy-1-methoxy-2,2,6,6-tetramethylpiperidine,
di-(1-methoxy-2,2,6,6-tetramethylpiperidin-4-yl) sebacate,
alpha,alpha'-(di-1-ethoxy-2,2,6,6-tetramethylpiperidin-4-yloxy)-p-xylene,
di-(1-benzyloxy-2,2,6,6-tetramethylpiperidin-4-yl) phthalate,
di-(1-benzyloxy-2,2,6,6-tetramethylpiperidin-4-yl)diethylmalonate
poly-{[6-1,1,3,3-tetramethylbutyl)-imino]-1,2,5-triazine-2,4-diyl][2-(1-cyclohexyloxy-2,2,6,6-tetramethylpiperidyl) -imino]-hexamethylene-[4-(1-cyclohexyloxy-2,2,6,6-tetramethylpiperidyl) -imino]},
(1-cyclohexyloxy-2,2,6,6-tetramethylpiperidin-4-yl)-3,5-di-t.butyl-4-hydroxybenzoate,
1-cyclohexyloxy-4-octadecanoyloxy-2,2,6,6-tetramethylpiperidine,
di-(1-methoxy-2,2,6,6-tetramethylpiperidin-4-yl)succinate,
di-(1-methoxy-2,2,6,6-tetramethylpiperidin-4-yl) isophthalate,
di-(1-cyclohexyloxy-2,2,6,6-tetramethylpiperidin-4-yl)sebacate,
di-(1-cyclohexyloxy-2,2,6,6-tetramethylpiperidin-4-yl)isophthalate,
4-benzoyloxy-1-(alpha-methylbenzyloxy)-2,2,6,6-tetramethylpiperdine,
di-[1-(alpha-methylbenzyloxy)-2,2,6,6-tetramethylpiperidin-4-yl]sebacate,
di-(1-heptyloxy-2,2,6,6-tetramethylpiperidin-4-yl)sebacate,
di-[1-(alpha-methylbenzyloxy)-2,2,6,6-tetramethylpiperidin-4-yl]aterephthalate,
di-(1-ethoxy-2,2,6,6-tetramethylpiperidin-4-yl)sebacate,
di-(1-cumyloxy-2,2,6,6-tetramethylpiperidin-4-yl)sebacate,
3,15-di-alpha-methylbenzyloxy-2,2,4,4,14,14,16,16-octamethyl-7,11,18,21-tetraoxa-3,15-diazatrispiro[5.2.2.5.2. 2]heneicosane, 3,15-dicyclohexyloxy-2,2,4,4,14,14,16,16-octamethyl-7,11,18,21-tetraoxa-3,15-diazatrispiro [5.2.2.5.2.2]heneicosane, di-(1-cyclohexyloxy-2,2,6,6-tetramethylpiperidin-4-yl)succinate, di-[1-alpha-methylbenzyloxy)-2,2,6,6-tetramethylpiperidin-4-yl]succinate, di-(1-nonyloxy-2,2,6,6-tetramethylpiperidin-4-yl)sebacate, di-(1-octadecyloxy-2,2,6,6-tetramethylpiperidin-4-yl) sebacate, di-(1-nonyloxy-2,2,6,6-tetramethylpiperidin-4-yl)succinate, di-[1-(1-methylcyclohexyloxy)-2,2,6,6-tetramethylpiperidin-4-yl]sebacate, di-[1-(3-cyclohexene-1-yloxy)-2,2,6,6-tetramethylpiperidin-4-yl]sebacate, di-(1-tert.butoxy-2,2,6,6-tetramethylpiperidin-4-yl)sebacate, di-(1-carbamoyloxy-2,2,6,6-tetramethylpiperidin-4-yl) n-butylmalonate, di-[1-(bicyclo-[4.4.0]-decyl-1-oxy)-2,2,6,6-tetramethylpiperidin-4-yl]sebacate, di-(1-n-butylcarbamoyloxy-2,2,6,6-tetramethylpiperidin-4-yl)phthalate, di-(1-n-butylcarbamoyloxy-2,2,6,6-tetramethylpiperidin-4-yl) n-butylmalonate, di-(1-phenylcarbamoyloxy-2,2,6,6-tetramethylpiperidin-4-yl) sebacate, 4-benzoyloxy-1-benzyloxy-2,2,6,6-tetramethylpiperidine, di-(1-octyloxy-2,2,6,6-tetramethylpiperidin-4-yl) sebacate, di-(1-benzyloxy-2,2,6,6-tyetramethylpiperidin-4-yl) sebacate, N, N', N'', N'''-tetrakis{2,4-bis[N-1-cyclohexyloxy-2,2,6,6-tetramethylpiperidin-4-yl)n-butylamino ]-1,3,5-triazin-6-yl}-3,3'-ethylenediiminodipropylamine, 2,4,6-tris[N-(1-cyclohexyloxy-2,2,6,6-tetramethylpiperidin-4-yl)-n-butylamino]-1,3,5-triazin, 2,4-bis[N-(1-cyclohexyloxy-2,2,6,6-tetramethylpiperidin-4-yl) -n-butylamino]-6-morpholino-1,3,5-triazine, N,N'-bis(1-cyclohexyloxy-2,2,6,6-tetramethylpiperidin-4-yl)-N,N═-bis {2,4-bis[N-(1-cyclohexyloxy-2,2,6,6-tetramethylpiperidin-4-yl)-n-butylamino]-1,3,5-triazin-6-yl}hexamethylene diamine, N,N'-bis{2,4-bis[N-(1-cyclohexyloxy-2,2,6,6-tetramethylpiperidin-4-yl) -n-butylamino]-1,3,5-triazin-6-yl}piperazine, N-(1-cyclohexyloxy-2,2,6,6-tetramethylpiperidin-4-yl) succinimide, N-(1-methoxy-2,2,6,6-tetramethylpiperidin-4-yl)n-dodecyl succinimide, tetrakis(1-octyloxy-2,2,6,6-tetramethylpiperidin-4-yl)-1,2,3,4-butanetetracarboxylate, and (1-methoxy-2,2,6,6-tetramethylpiperidin-4-yl)(1-octyloxy-2,2,6,6-tetramethylpiperidin-4-yl)sebacate.

3. The composition of claim 1, wherein $R_1$ is

4. The composition of claim 3, wherein said compound is (1-acetoxy-2,2,6,6-tetramethylpiperidin-4-yl)-4-hydroxy-3,5-di-tert-butylbenzoate.

5. The composition of claim 3. wherein said compound is di-(12-acetoxy-2,2,6,6-tetramethylpiperidin-4-yl)sebacate.

6. The composition of claim 3, wherein said compound is 2-)4-hydroxy-3,5-di-tert.butylbenzyl)-2-(1-acetoxy-2,2,6,6-tetramethylpiperdin-4-yl) n-butylmalonate.

7. The composition of claim 2, wherein said compound is di-(1-cyclohexyloxy-2,2,6,6-tetramethylpiperdin-4-yl)sebacate.

8. The composition of claim 2, wherein said compound is di-(1-heptyloxy-2,2,6,6-tetramethylpiperdin-4-yl)sebacate.

9. The composition of claim 2, wherein said compound is di-(1-methoxy-2,2,6,6-tetramethylpiperdin-4-yl)sebacate.

10. The composition of claim 2, wherein said compound is di-(1-nonyloxy-2,2,6,6-tetramethylpiperdin-4-yl)sebacate.

11. The composition of claim 2, wherein said compound is di-[1-(alpha-methylbenzyloxy)-2,2,6,6-tetramethylpiperdin-4-yl]sebacate.

12. The composition of claim 3, wherein said compound is di-(1-benzoyloxy-2,2,6,6-tetramethylpiperdin-4-yl) sebacate.

13. The composition of claim 2, wherein said compound is di-(1-benzyloxy-2,2,6,6-tetramethylpiperdin-4-yl) sebacate.

14. The composition of claim 2. wherein said compound is di-[1-(alpha-methylbenzyloxy)-2,2,6,6-tetramethylpiperidin-4-yl]terephthalate.

15. The composition of claim 3, wherein said compound is di-(1-n-butylcarbamoyloxy-2,2,6,6-tetramethylpiperidin-4-yl) n-butylamalonate.

16. The composition of claim 2, wherein said compound is di-(1-ethoxy-2,2,6,6-tetramethylpiperdin-4-yl)sebacate.

17. The composition of claim 2, wherein said compound is di-(1-octyloxy-2,2,6,6-tetramethylpiperdin-4-yl) sebacate.

18. The composition according to claim 1, wherein the compound of component (b) is contained in an amount of 0.1 to 5% by weight, based on resin solids.

19. The composition according to claim 1 which additionally contains a UV absorber selected from the group consisting of benzophenones, benzotriazoles, acrylic acid derivative, aryl-s-triazines, organic nickel compounds and oxanilides.

20. A composition according to claim 18 which contains a benzotriazole UV absorber selected from the group consisting of 2-[2-hydroxy-3,5-di(alpha,alpha-dimethyl-benzyl) phenyl]-2H-benzotriazole, 2-(2-hydroxy-3,5-di-tert-octylphenyl) -2H-benzotriazole, 2-(2-hydroxy-3-alpha,alpha-dimethylbenzyl-5-tert-octylphenyl) -2H-benzotriazole, 2-(2-hydroxy-3-tert-octyl-5-alpha,alpha-dimethylbenzylphenyl) -2H-benzotriazole, 2-[2-hydroxy-3-tert-butyl-5-(2(omega-hydroxy-octa(ethyleneoxy) carbonyl)ethylphenyl]-2H-benzotriazole, 2-(2-hydroxy-3,5-di-tert-amylphenyl) -2H-benzotriazole, dodecylated 2-(2-hydroxy-5-methylphenyl) -2H-benzotriazoles, 5-chloro-2-[2-hydroxy-3,5-di(alpha,alpha-dimethylbenzyl) -phenyl]-2H-benzotriazole, 5-chloro-2-(2-hydroxy-3-alpha,alpha-dimethylbenzyl-5-tert-octylphenyl) -2H-benzotriazole, 5-chloro-2-(2-hydroxy-3-tert-octyl-5-alpha,alpha-dimethylbenzylphenyl) -2H-benzotriazole, 5-chloro-2-[2-hydroxy-3-tertbutyl-5-(2-(omega-hydroxyocta-(ethyleneoxy) -ethylphenyl]-2H-benzotriazole, 5-chloro-2-(2- hydroxy-5-tert-octylphenyl) -2H-benzotriazole, 5-chloro-2-(2-hydroxy-3,5-diatert-amylphenyl) -2H-benzotriazole, and 5-chloro-2-[2-hydroxy-3-tert.butyl-5-(2-octyloxycarbonyl) ethylphenyl]-2H-benzotriazole.

21. A composition according to claim 20, wherein the benzotriazole is 2-[2-hydroxy-3,5-di(alpha,alpha-dimethylbenzyl) -phenyl]-2H-benzotriazole, 2-[2-hydroxy-3-tert.-butyl-5-(2-(omega-hydroxy-octa(ethyleneoxy) carbonyl)-ethylphenyl]-2H-benzotriazole, 2-[2-hydroxy-3-tert.butyl-5-(2-octyloxycarbonyl) ethylphenyl]-2H-benzotriazole or 5-chloro-2-[2-hydroxy-3-tert.butyl-5-(2-octyloxycarbonyl) ethylphenyl]-2H-benzotriazole.

22. The composition according to claim 19, wherein the total amount of component (b) plus UV absorber is 0.2 to 20% by weight based on the resin solids.

23. The composition according to claim 19, which additionally contains a phosphite or phosphonite antioxidant.

24. The composition according to claim 23 which additionally contains a hindered phenol antioxidant.

25. The composition according to claim 1 which is an enamel of high solids content for industrial finishes.

26. The composition according to claim 1 which is a finishing enamel for automobiles.

27. The composition according to claim 1 which is a coil coating.

* * * * *

UNITED STATES PATENT AND TRADEMARK OFFICE
CERTIFICATE OF CORRECTION

PATENT NO. : 5,112,890
DATED : May 12, 1992
INVENTOR(S) : Behrens et al.

Page 1 of 1

It is certified that error appears in the above-identified patent and that said Letters Patent is hereby corrected as shown below:

Title page, left column delete section [*] regarding a terminal disclaimer in its entirety.

Signed and Sealed this

Seventh Day of August, 2001

Attest:

*Nicholas P. Godici*

Attesting Officer

NICHOLAS P. GODICI
*Acting Director of the United States Patent and Trademark Office*